US00PP37182P2

(12) United States Plant Patent
Braun et al.

(10) Patent No.: US PP37,182 P2
(45) Date of Patent: Dec. 30, 2025

(54) ***CORYLUS* PLANT NAMED 'STAPN7-6'**

(50) Latin Name: ***Corylus* hybrid**
Varietal Denomination: StapN7-6

(71) Applicants: REGENTS OF THE UNIVERSITY OF MINNESOTA, Minneapolis, MN (US); WiSys Technology Foundation, Madison, WI (US)

(72) Inventors: Lois Caroline Braun, Falcon Heights, MN (US); Jason Allen Fischbach, Ashland, WI (US)

(73) Assignees: WISYS TECHNOLOGY FOUNDATION, INC., Madison, WI (US), PART INTEREST; REGENTS OF THE UNIVERSITY OF MINNESOTA, Minneapolis, MN (US), PART INTEREST ( * ) Notice: Subject to any disclaimer, the term of this patent is extended or adjusted under 35 U.S.C. 154(b) by 0 days.

(21) Appl. No.: 18/985,035

(22) Filed: Dec. 18, 2024

Related U.S. Application Data

(60) Provisional application No. 63/612,392, filed on Dec. 20, 2023.

(51) Int. Cl.
*A01H 5/08* (2018.01)
*A01H 6/00* (2018.01)

(52) U.S. Cl.
USPC ..... Plt./152
CPC ..... *A01H 6/00* (2018.05)

(58) Field of Classification Search
USPC ..... Plt./152
CPC ..... A01H 5/0825
See application file for complete search history.

*Primary Examiner* — Kent L Bell
(74) *Attorney, Agent, or Firm* — Penny J. Aguirre

(57) ABSTRACT

The invention is a new and distinct variety of *Corylus* plant named 'StapN7-6' that is characterized by its yield of up to nine nuts per cluster (average 4.1/cluster) on terminal stems that are primarily visible outside of the plant's foliage, its relatively medium plant stature and highly suckering and sprawling form, its mid-to late season maturing nut season; maturing in late August to early September in Minnesota, its moderately high nut yields of 294 g of kernel/plant, an average shell-out rate of 34% and an average kernel weight of 0.56 g, its average Modal in-shell nut diameter of 1.6 cm with an average kernel diameter of 1.1 cm, its kernels that are relatively clean of skin and fiber, its in-shell nut sphericity of 91 and a kernel sphericity of 87, and its cold hardiness at least to U.S.D.A. Zone 4b.

3 Drawing Sheets

CROSS-REFERENCE TO A RELATED APPLICATION

This application claims priority to a U.S. Provisional Patent Application, Application No. 63/612,392 filed Dec. 20, 2023 under 35 U.S.C. 119(e), the entire contents of which is incorporated by reference herein.

STATEMENT REGARDING FEDERALLY SPONSORED RESEARCH

This invention was made with government support under LNC15-367, LNC10-328, and SCBG 18-18 awarded by the National Institute of Food and Agriculture/Sustainable Agriculture Research and Education and 2011-51181-30681, and 2019-51181-30025 awarded by the National Institute of Food and Agriculture. The government has certain rights in the invention.

Botanical classification: *Corylus* hybrid.
Variety denomination: 'StapN7-6'.

BACKGROUND OF THE INVENTION

The present invention relates to a new and distinct cultivar of *Corylus* plant of hybrid origin and botanically known as *Corylus* 'StapN7-6', referred to hereafter by its cultivar name, 'StapN7-6'.

The new cultivar arose as part of breeding initiative that commenced in 2006 for improved hazelnut germplasm for the upper Midwest based on interspecific hybrids between *Corylus americana, Corylus avellana*, and other species. 'StapN7-6' was selected as a seedling by one of the Inventors that was growing in an evaluation field in Staples, Minnesota in 2005. The seedling was selected from seed planted in 2000 from open pollination of unnamed and unpatented plants. The seeds were pooled from the open pollinations and therefore the parents plants are unknown. Subsequent evaluations were done in 5 locations in Minnesota and Wisconsin for the new cultivar's suitability for growing in the upper Midwest. Characteristics evaluated included kernel yields, kernel quality, winter hardiness, and disease resistance.

Asexual propagation of the new cultivar was first accomplished by mound layering in 2011 by one of the Inventors in Staples, Minnesota. Asexual propagation of the new cultivar by mound layering and stem cuttings has determined that the characteristics are stable and true to type in successive generations.

SUMMARY OF THE INVENTION

The following traits have been repeatedly observed and represent the characteristics of the new cultivar. These attributes in combination distinguish 'StapN7-6' as a new and unique cultivar of *Corylus*.

1. 'StapN7-6' exhibits up to nine nuts per cluster (average 4.1/cluster) on terminal stems that are primarily visible outside of the plant's foliage.
2. 'StapN7-6' exhibits a relatively medium plant stature and highly suckering resulting in a sprawling form.
3. 'StapN7-6' exhibits a mid to late-season maturing nut season; maturing in late August to early September in Minnesota.
4. 'StapN7-6' exhibits moderately high nut yields of 294 g of kernel/plant, an average shell-out rate of 34% and an average kernel weight of 0.56 g.
5. 'StapN7-6' exhibits an average Modal in-shell nut diameter of 1.6 cm with an average kernel diameter of 1.1 cm.
6. 'StapN7-6' exhibits kernels that are relatively clean of skin and fiber.
7. 'StapN7-6' exhibits an in-shell nut sphericity of 91 and a kernel sphericity of 87.
8. 'StapN7-6' exhibits cold hardiness at least to U.S.D.A. Zone 4b.

'StapN7-6' can be compared to the *Corylus* hybrid cultivars 'Northern Blais' (not patented) and 'Marion' (not patented), which are both similar to 'StapN7-6' in having hardiness to at least U.S.D.A. Zone 4b and kernels that lack fiber or skin and both differ in being hybrids derived from different species than 'StapN7-6'. However, 'Northern Blais' differs from 'StapN7-6' in that is a hybrid derived from *C. avellana* and *C. heterophylla*, whereas 'StapN7-6' is derived primarily from *C. avellana* and *C. americana*. 'Northern Blais' differs from 'StapN7-6' in having in-shell nuts and kernels that are larger in size and prolate in shape, nut shells that are slightly pink in color and are thicker, nuts that are hidden under the foliage, a lower nut yield, more upright growth habit, and foliage that stays green longer into autumn. 'Marion' differs from 'StapN7-6' in having in-shell nuts and kernels that are larger in size, nut shells that are thinner, nuts that are hidden under the foliage with fewer nuts per clusters and lower yield, a more upright growth habit, and foliage that stays green into autumn.

STATEMENT REGARDING PRIOR DISCLOSURES BY THE INVENTORS

The Applicants assert that no publications or advertisements relating to sales, offers for sale, or public distribution occurred more than one year prior to the effective filing date of this application. Any information about the claimed plant would have been obtained from a direct or indirect disclosure from the Inventors. The Applicants claim a prior art exemption under 35 U.S.C. 102(b)(1) for disclosure and/or sales prior to the filing date but less than one year prior to the effective filing date. Disclosures related to research trials without any offers for sale include website listings by American Society for Horticultural Science, USDA REEIS, Iowa State University, University of Minnesota, Midwest Winepress, University of Wisconsin, American Journal of Enology and Viticulture.

BRIEF DESCRIPTION OF THE DRAWINGS

The accompanying color photographs illustrate the overall appearance and distinct characteristics of the new *Corylus*. The photographs were taken on plants 14 years in age as produced by mound layering and grown outdoors in a trial field in Falcon Heights, Minnesota.

The photograph in FIG. 1 provides a side view of 'StapN7-6' in late spring.

Figure 1:
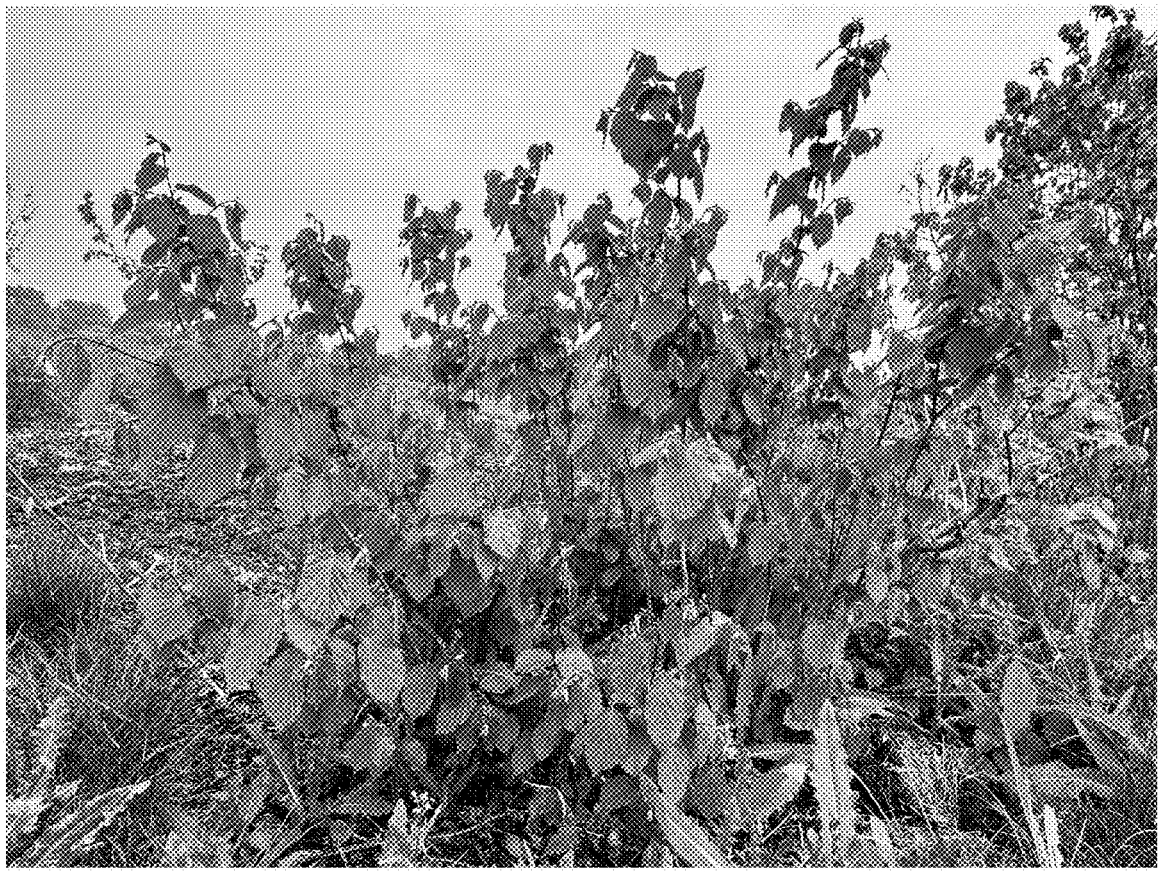
Figure 2:
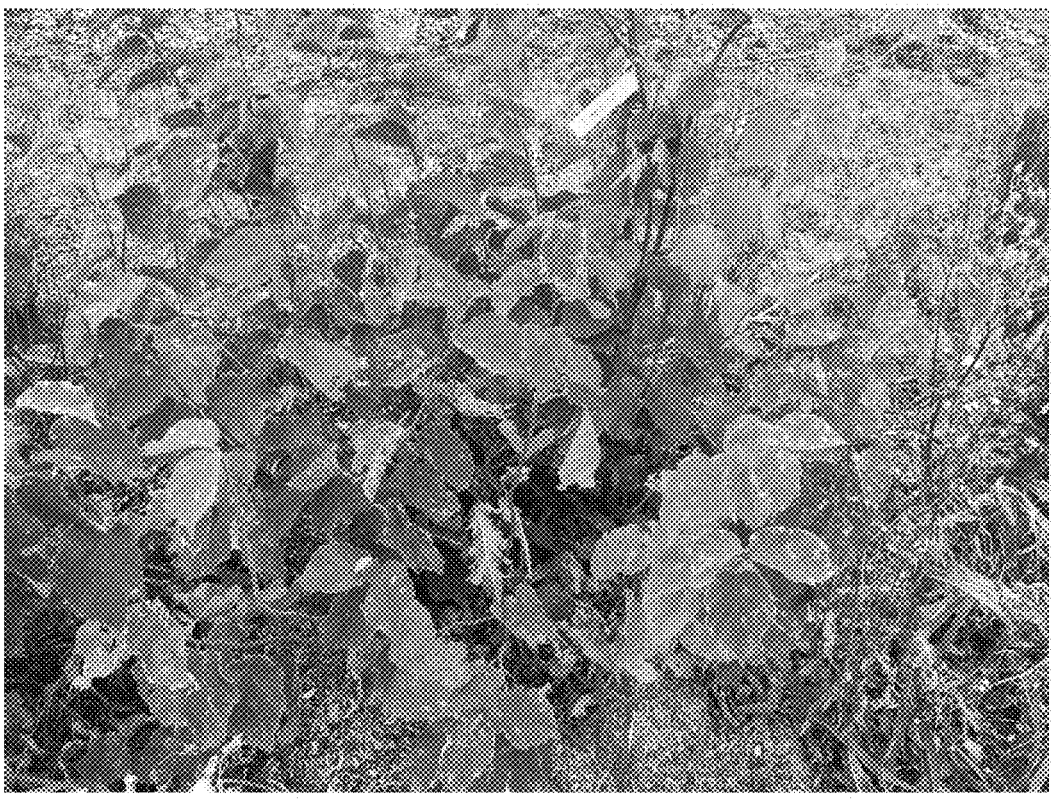

The photograph in FIG. 2 provides a view of the fall foliage of 'StapN7-6'.

Figure 3:
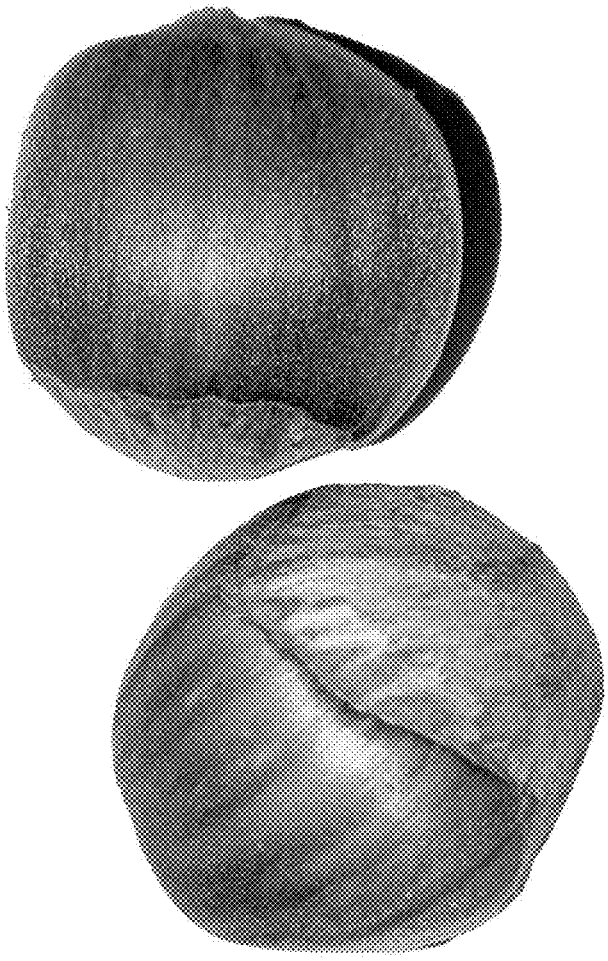

The photograph in FIG. 3 provides a view of the nuts of 'StapN7-6'.

The colors in the photographs are as close as possible with the photographic and printing technology utilized and the values cited in the detailed botanical description accurately describe the colors of the new *Corylus*.

DETAILED BOTANICAL DESCRIPTION

The following is a detailed description of 9-year-old plants of the new cultivar as produced by mound layering and grown in a trial field in Falcon Heights, Minnesota. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Mid-March to early May in Falcon Heights, MN.

*Plant type*.—Deciduous, nut producing perennial shrub.

*Plant habit*.—Medium statured, sprawling, highly suckering.

*Height and spread*.—Average of 2.7 m in height and about 1.50 m in width as a 9-year-old plant in the field.

*Cold hardiness*.—At least to U.S.D.A. Zone 4b.

*Diseases and pests*.—Has shown resistance to Eastern filbert blight (caused by *Annisogramma anomala*), no susceptibility or resistance to other diseases or pests has been observed.

*Root description*.—Fine, freely branched, 178B and 203B in color.

*Propagation*.—Stem cuttings and mound layering.

*Root development*.—Juvenile cuttings from a coppiced plant root in as little as one month.

*Growth rate*.—Slow, nuts are typically produced by the fifth field season.

Branch description:

*Branch shape*.—Rounded, strong.

*Branch color*.—Emerging; 187A, young; N199B and 201A, mature; N200A to N200B, old bark; 202C.

*Branch size*.—Lateral branches; average 60 cm in length, 1 cm in diameter, tertiary branches; 10 cm in length, 5 mm in diameter, main branch; 67 cm in length, trunk 4 cm in diameter.

*Stem surface*.—Matte with a slight luster in the sun, moderately covered with lenticels, average of 0.5 mm in length and width, rounded in shape, NN155A in color.

*Branching*.—1 main branch (trunk), average of 8 lateral branches and suckers, 4 tertiary branches per lateral branch.

*Branch internode length*.—Average of 2.5 cm.

Leaf description:

*Leaf shape*.—Narrowly cordate.

*Leaf apex*.—Acute to apiculate.

*Leaf base*.—Cordate.

*Leaf margins*.—Serrate, unlobed.

*Leaf color*.—Newly expanded leaves both surfaces; 184A and 183A with undertones of 144B, young leaves upper and lower surface; a blend of 199A and 176A, with undertones of 144B, mature upper and lower surface; 144B, becoming flushed with a very light hint of 199A as the leaves age, fall foliage; both surfaces a blend of N34B, N34C, 16C, N144B, 183A throughout the fall season.

*Leaf veins*.—Pinnate, both surfaces match leaf color, 150C, fall foliage; matches leaf color description.

*Leaf size*.—5.5 cm in length, 3 cm in width.

*Leaf surface*.—Both surfaces matte and are densely covered with minute soft hairs that feel velvety to the touch, hairs match leaf color, too small to measure.

*Petioles*.—Average of 8 mm in length and 3 mm in width, colors; emerging 187A, young and mature; 144A, both surfaces are moderately to densely covered with pubescent hairs, 1 mm in length, hair colors; emerging 187B, young and mature 184A.

*Stipules*.—2 per petiole, leafy and drop when the leaf matures, ovate in shape, acuminate apex, cuneate base, average of 6 mm in length and 2.5 mm in width, 144A, tips flushed with 183A, matte surface, serrated margins.

Flower description:

*Flower type*.—Imperfect, monoecious.

*Flowers* (*female, pistillate*).—Average of 25 per plant, 6 mm in length, 4.5 mm in diameter, en masse a blend of 177A and 195A in color, oval in shape, matte surfaces, stigmatic styles; hair-like, average of 25, 3.5 mm in length, 0.4 mm in width, matte, glabrous surface, color; 60C, fading to 203A.

*Flower fragrance*.—None.

*Flower buds*.—(Female flowers only) 1.2 cm in length, 6 mm in width, oblong in shape.

*Bud scales*.—Buds covered with bud scales; 4 to 8, color; surfaces 144B in color, tips and margins N199B in color.

*Sepals*.—Average of 6, whorled, 2 mm in length, 3 mm in width, acute apex, cuneate base, cupped in shape, upper and lower surface matte, margins entire and slightly translucent, colors; 200B, tip and margins 194A.

*Catkin* (*male, staminate*).—Pendulous and cylindrical in shape, an average of 25 per plant, an average of 3.5 cm in length and 3 mm in diameter, peduncles; 5 mm in length, 1 mm in width, matte and glabrous surface, curved downward from stem, 165A in color scales; winged, deltoid in shape, an average 2 mm in length and 3 mm in width, apex; cuspidate, base; acute, color; upper surface 165A and 201A, lower surface 164A, en masse; surface is scaly in appearance and whorled, matte luster, an average of 250 flowers per catkin, pedicels; very small, 0.5 mm in length and width, glabrous surface, held vertical in angle to peduncle, 164A in color, stamens; average of 12 per winged scale, 0.5 mm in diameter, deltoid in shape, color; 164A, filament; barely visible, dry, 164A in color, 0.4 mm in length, pollen; abundant, 22B in color.

*Husk description* (*involucre bracts*).—Each nut is wrapped in 2 husks, 2 cm in length, 2.7 cm in width, strong and hard to tear, leaf-like, broadly ovate in shape, base; broadly cuneate, apex; overall square in shape, margins; undulate and irregularly serrate, shallow sinus depth between ridges, acute apexes, surfaces; young outer surface is satiny, matte and densely covered with tomentose translucent hairs that match the surface color, young inner surface is glossy, satiny, and densely covered with tomentose hairs that match the surface color, mature inner and outer surfaces are matte, dry, rugose, and papery, color; young inner and outer surface 145B, mature outer surface 145D, mid-section 165A, mature inner surface 145D.

Nut description:

*Maturation date*.—Mid to late-season; late August to early September in Minnesota.

*Nuts ripening time*.—Average of 42 days.

*Nuts per cluster*.—Up to nine (average 4.1).

*Cluster size*.—6 cm in depth, 7 cm in width.

*Cluster weight*.—16 g.

*Nut size*.—1.6 cm in depth and diameter, thickness 4 mm.

*Nut shape*.—Nearly spherical; in shell sphericity 91.

*Nut weight*.—1.3 g.

*Nut surface*.—Top half of nut; glabrous, matte, slightly rugose, bottom half of nut; glabrous, very smooth with a lustrous sheen.

*Nut color*.—Top half of nut; striations of NN155D and 155A, bottom half of nut; a blend of 174A and 175A, average number of striations is 20.

*Nut apex*.—Rounded, slightly pointed.

*Inside of nut shell*.—Exfoliating and striate, 176B in color, glossy.

*Nut yield*.—Moderately high, average of 294 g kernel/plant, density of 98 g kernel $m^{-2}$, average shell-out rate 34% shell-out rate.

*Nut bearing*.—Alternative.

*Nut basal scar curvature*.—Slight, indented to flat.

*Nut pistil scar on shell*.—Slight, linear and slightly raised, 0.3 mm in depth, 5 mm in width.

Kernel description:

*Kernel size*.—1.1 cm in depth and diameter.

*Kernel quantity*.—1.

*Kernel shape*.—Spherical.

*Kernel weight*.—0.56 g.

*Kernel surface*.—Striate, slightly glossy, smooth, lateral groove present.

*Kernel skin*.—Relatively clear of skin and fiber color matches kernel color 158C.

*Kernel color*.—158C.

*Kernel apex*.—Not prominent.

It is claimed:

1. A new and distinct variety of *Corylus* plant named 'StapN7-6' as described and illustrated herein.

* * * * *